US006973842B1

(12) United States Patent
Feller

(10) Patent No.: US 6,973,842 B1
(45) Date of Patent: Dec. 13, 2005

(54) FLOW PROBE PIPE SIZE DETECTOR

(76) Inventor: Murray F. Feller, 21577 NW. 75th Avenue Rd., Micanopy, FL (US) 32667

( * ) Notice: Subject to any disclaimer, the term of this patent is extended or adjusted under 35 U.S.C. 154(b) by 10 days.

(21) Appl. No.: 10/946,834

(22) Filed: Sep. 22, 2004

(51) Int. Cl.[7] ................................. G01F 1/66
(52) U.S. Cl. .................. 73/861.27; 73/597; 73/610
(58) Field of Search .................. 73/861.27, 861.26, 73/861.28, 861.29, 597, 598, 602, 610

(56) References Cited

U.S. PATENT DOCUMENTS

| 6,178,827 B1 | 1/2001 | Feller |
| 6,345,539 B1 | 2/2002 | Rawes et al. |
| 6,422,093 B2 | 7/2002 | Feller |
| 6,457,371 B1 | 10/2002 | Feller |
| 6,474,165 B1 * | 11/2002 | Harper et al. ................. 73/623 |
| 6,508,134 B1 | 1/2003 | Feller |
| 6,530,285 B1 | 3/2003 | Feller |
| 6,584,860 B1 | 7/2003 | Feller et al. |
| 6,739,203 B1 | 5/2004 | Feldman et al. |

* cited by examiner

Primary Examiner—Harshad Patel
(74) Attorney, Agent, or Firm—David Kiewit

(57) ABSTRACT

An acoustic time-of-flight size measuring device is added to the sensing head of an insertion probe sensor which may be used for measuring the flow of fluid in a pipe. The size-measuring device defines an acoustic beam making a plurality of reflective contacts with the pipe's interior wall. A time-of-flight measurement of this path length provides an accurate measurement of the internal diameter of the pipe. The magnitude of the transit time signal can also be used as an indicator of both insertion depth and angular orientation of the probe with respect to the pipe axis. In addition, the arrangement allows one to sense acoustic path attenuation caused by factors such as the buildup of deposits.

25 Claims, 2 Drawing Sheets

FLOW PROBE PIPE SIZE DETECTOR

BACKGROUND OF THE INVENTION

1. Field of the Invention

The present invention relates to apparatus and methods of compensating for the variation of internal diameters of pipes in which sensing probes are inserted, optimizing their insertion depth and orientation during installation, and detecting the accumulation of pipe wall deposits.

2. Background Information

Insertion probes for detecting the flow of fluids are typically mounted in round pipes having internal diameters that are not precisely known. Because these probes are generally used to measure flow rate by sampling a small portion of the flow profile and deriving from that measurement the volumetric flow rate based upon an assumed internal pipe diameter, a pipe diameter different from that assumed can introduce significant error into the derived results.

The magnitude of the problem can be seen by considering the ASTM A 106 dimensional limits for a range of diameters about a nominal diameter of six inches for schedule 40 steel pipe. The tolerances are +1/16", -1/32" in diameter and +15%, -12.5% in wall thickness. The corresponding variation in wetted cross sectional area approaches 2% and provides that degree of uncertainty in determining volumetric flow rate. Those skilled in the art will recognize that tolerances vary with the pipe size and may increase or decrease from the recited example.

The potential error related to this variation in internal diameter has not received much attention in the past because of the acceptance of the probe type of flow sensing instrument as one of relatively low accuracy and because of the difficulty in measuring the internal diameter of installed pipes. There is, however, an increasing demand for improved performance, which indicates that a practical means of compensation for diameter variations is desired.

Insertion probes generally need to be inserted to a correct depth and to have a precise angular orientation with respect to the direction of the flowing fluid in order to minimize flow measurement error. Feldman et al., in U.S. Pat. No. 6,584,860, the disclosure of which is herein incorporated by reference, teach methods of and apparatus for measuring a distance between a portion of the insertion probe and a portion of the piping apparatus into which it is inserted, as well as for combining the results of these measurements with a presumed pipe diameter in order to insert the probe to the correct depth.

Accumulation of scale and other deposits on the inside walls of pipes through which fluids flow can significantly change the effective diameter of the pipe and also inhibit flow near the pipe walls so as to cause a change in the flow profile through the pipe. This is a recognized problem that is not solved by the prior art of using a single, pre-set diameter through the service life of a given flow sensor.

BRIEF SUMMARY OF THE INVENTION

In one embodiment of the present invention, a probe-type flow sensor is improved by adding an acoustic time-of-flight size measuring device to the sensing head. In a preferred arrangement of this sort a transmitting transducer directs an acoustic beam so as to make a plurality of reflective contacts with the pipe's interior wall prior to reaching a receiving transducer. This arrangement provides for an accurate measurement of the internal diameter (ID) of the pipe and also enables the magnitude of the received acoustic signal to be used as an indicator of both insertion depth and angular orientation with respect to the pipe axis. In addition, the arrangement provides a means for sensing acoustic path attenuation caused by factors such as the buildup of deposits. This method differs from that taught by Feldman et al. in U.S. Pat. No. 6,584,860 in that the pipe ID is actually measured, rather than taking Feldman et al.'s approach of assuming that a nominal pipe ID is equal to the actual one.

In one preferred embodiment of the present invention the acoustic distance measuring device is attached to the flow sensing probe so that when the flow sensing head is oriented with its axis of measurement aligned with the axis of the pipe, the acoustic measuring device is positioned to transmit and receive its acoustic signals perpendicular to the pipe axis. In a fluid-filled pipe these acoustic waves are multiply reflected by the pipe wall and propagated along chordal paths through the cross section of the pipe. Because the acoustic transit time is proportional to the ID of the pipe, this allows for measurement of the pipe ID, which is then used to adjust the calibration of the flow rate measurement by replacing a nominal pipe ID value with the measured one. This, of course, may be either a manual adjustment or an automatic trimming of the flow sensor's span calibration. Moreover, the magnitude of the signal detected by the receiving transducer of the acoustic distance measuring device is an indication of the optimization of the acoustic path and of possible presence of scale or other internal deposits. When this preferred probe is adjusted to the optimum depth and orientation angle, the signal has a maximum level. By adjusting the probe mounting during its installation for this maximum level, an installation is made which more closely approximates the factory calibration conditions than that which would result if the installer merely used relatively crude mechanical measurements and his visual aiming abilities to set insertion depth and orientation. To facilitate this calibration, the flow sensing probe may contain a display device such as an analog or digital voltmeter or array of LEDs to indicate the received signal level.

Transit times can be measured for many chordal paths, and the results used with well known geometric relationships to calculate the pipe ID. In one preferred embodiment transmitting and receiving transducers respectively project and receive an acoustic beam oriented perpendicular to the probe insertion axis, and the insertion depth of the transducers is selected to be 25% of the pipe's inside diameter. This defines a multi-segmented chordal acoustic path that is an equilateral triangle disposed in a plane perpendicular to an axis of the pipe. This use of three equidistant acoustic reflection locations on the pipe wall represents a good compromise between factors such as signal strength, which generally diminishes with an increasing number of reflections, and the precision of diametric measurement which generally increases with an increasing number of reflections. In addition, other tests have shown that when a probe projecting a beam perpendicular to the axis of the probe is inserted 13.3% of the pipe diameter, the muti-segmented path has a square shape. It may be noted that in order to accommodate a wide range of pipe sizes with a single size of flow sensing probe, the location of the transducers on the probe or the angle of the beam with respect to the probe axis may need to be modified to optimize the probe depth at which the received acoustic signal magnitude is a maximum.

The present invention is compatible with different types of probes because it can operate independently and requires little additional space on the probe for its implementation.

Although it is believed that the forgoing recital of features and advantages may be of use to one who is skilled in the art and wishes to learn how to practice the invention, it will be recognized that the foregoing recital not intended to list all of the features and advantages. Moreover, it may be noted that various embodiments of the invention may provide various combinations of the herein before recited features and advantages of the invention, and that less than all of the recited features and advantages may be provided by some embodiments.

BRIEF DESCRIPTION OF THE SEVERAL VIEWS OF THE DRAWING

The various advantages of the present invention will become apparent to one skilled in the art by reading the following specification and subjoined claims and by referencing the following drawings in which:

DETAILED DESCRIPTION OF THE INVENTION

Figures 1, 2, 3:
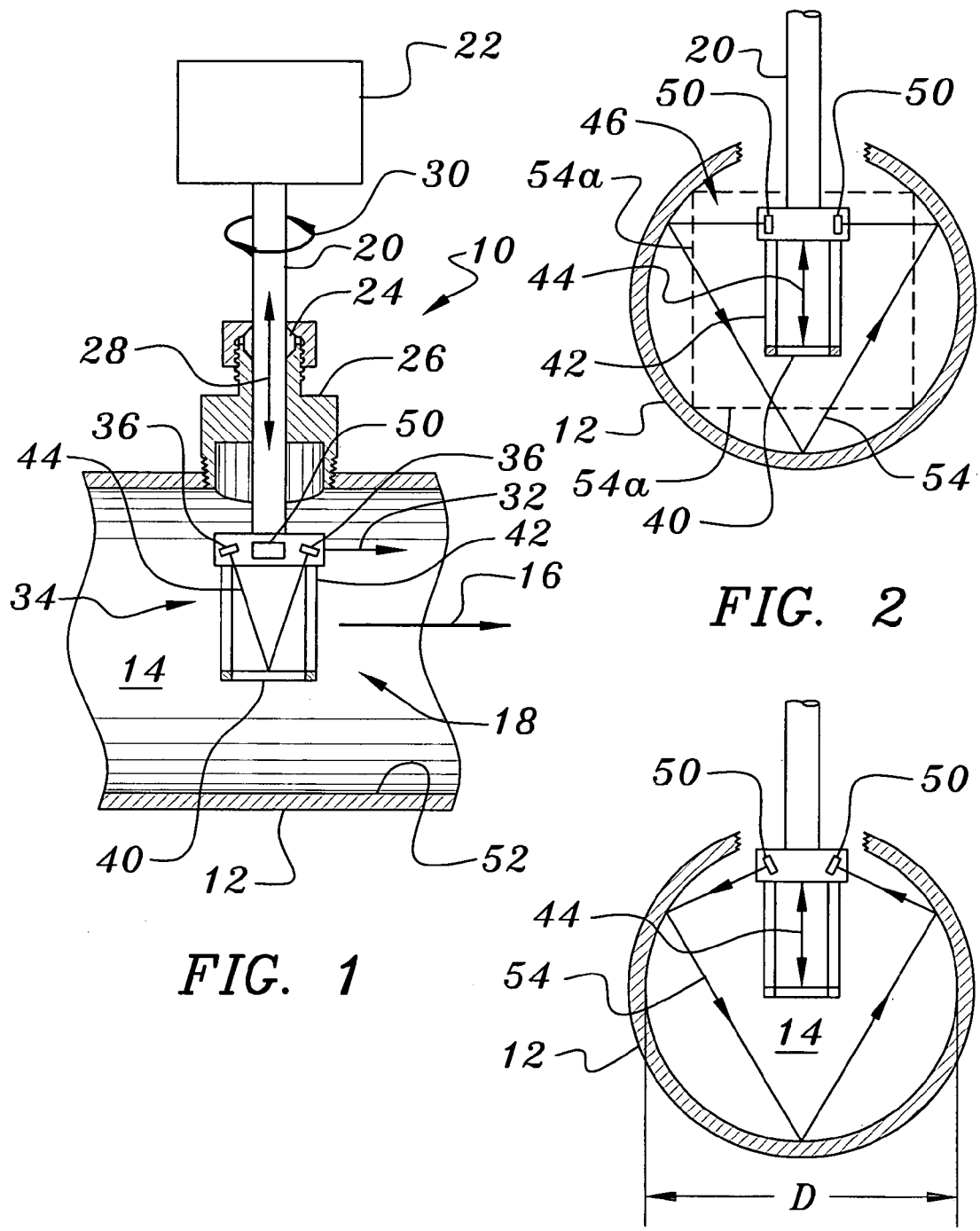
FIG. 1 is a partly schematic vertical sectional view, taken along an axis of a pipe, of a preferred embodiment of an insertion probe for measuring both pipe size and flow.
FIG. 2 is a partial sectional view, taken perpendicular to the axis of the pipe, of the preferred embodiment of FIG. 1.
FIG. 3 is a partial sectional view, similar to that of FIG. 2, but depicting an alternate acoustic measurement path defined by one or more angled transducers.

In studying this Detailed Description, the reader may be aided by noting definitions of certain words and phrases used throughout this patent document. Wherever those definitions are provided, those of ordinary skill in the art should understand that in many, if not most instances, such definitions apply to both preceding and following uses of such defined words and phrases. At the outset of this Description, one may note that the terms "include" and "comprise," as well as derivatives thereof, mean inclusion without limitation; and the term "or," is inclusive, meaning and/or.

The term "insertion probe" as used herein, denotes an elongated member designed to be inserted into a pipe or other vessel so that a sensing element on, or closely adjacent, the inserted end of the probe is at a selected insertion depth. More specifically, a "flow probe", as used herein, provides the conventional denotation of a portion of a flow sensor configured to be inserted into a pipe. A "flow velocity detector", as used herein, is any sort of device mounted on a flow probe to provide an electrical signal output (hereinafter "raw flow signal") that is a measure of the rate at which fluid flows along a predetermined "flow measurement direction" defined with respect to the flow probe. When the flow probe is inserted into a pipe so that the flow measurement direction is parallel to or co-linear with an axis of the pipe, the raw flow signal is then a measure of the rate at which fluid is flowing past the probe at whatever insertion depth has been selected. In many cases what is desired is the volumetric flow rate (e.g., gallons per minute), which is calculated by multiplying the fluid flow rate by the cross-sectional area of the inside of the pipe. Thus, a "volumetric flow sensor" is an instrument having an output representative of the volumetric flow rate. As noted previously, prior art volumetric flow sensors generally operate by assuming a nominal value of the inside diameter ("ID") of a pipe and using that value to calculate the cross-sectional flow area. In large pipes having a smooth inside surface one commonly finds that a flow velocity detector inserted to 11% of the ID of the pipe will provide an output representative of volumetric flow over a wide range of flow rates. If one is dealing with smaller pipes or with pipes having a rough internal surface, a somewhat deeper insertion depth is typically desired. Thus, regardless of what insertion depth is nominally selected it will be understood that installation of a flow probe comprises both inserting the probe to the selected insertion depth and turning the probe about its axis until the predetermined flow sensing direction is parallel to the pipe axis.

Several embodiments of the invention are depicted in the various figures of the drawing. A common setting for the drawing shows a transducer probe inserted through a probe insertion fitting extending upwards from the top of the pipe as a matter of convenience. Those skilled in the art will recognize that other insertion orientations may equally well be used. Moreover, directional terms such as "up" and "down" in the subsequent disclosure are used with reference to the depicted orientation in the interest of more clearly explaining the invention, and are not to be taken as limiting the invention to any particular setting.

As noted previously, one aspect of the present invention comprises improving a probe-type flow sensor by adding an acoustic distance measuring device to the sensing head in order to increase the accuracy of the flow measurement by providing an accurate measure of a pipe's internal diameter.

Turning now to FIG. 1, one finds an insertion probe sensor 10 in accordance with a preferred embodiment of the present invention as it would be typically mounted in a pipe 12 containing a fluid 14 flowing along an axis 16 of the pipe 12. As is conventional in the use of insertion probes, the depicted sensing head 18 is supported by a hollow stem 20 that serves as a conduit for wires (not shown) coupling the sensing devices to associated electronic circuitry 22. The depicted stem 20 passes through a shaft seal 24 portion of a conventional insertion fitting 26. During installation of the probe sensor 10, the shaft seal 24 can be loosened to allow an operator to move the stem 20 into and out of the pipe (as depicted by the double-headed straight arrow 28 in FIG. 1) and to rotate the stem about its axis (as depicted by the double headed arcuate arrow 30 in FIG. 1) into a selected rotational setting about the probe axis. As will be discussed in greater detail hereinafter, these adjustments are important to assure that the sensing head 18 is disposed at a desired insertion depth, and that the flow measurement direction (indicated with an arrow 32 in FIG. 1) of the sensing head 18 is parallel to or coincident with the axis 16 of the pipe. Those skilled in the flow measurement arts will recognize that many mechanisms and approaches can be used to make these two settings.

A preferred flow rate detector 34 is of the ultrasonic transit-time type taught in Feller's U.S. Pat. Nos. 6,422,093, 6,457,371 and 6,508,134. This flow rate detector comprises a pair of flow-measuring piezoelectric transducers 36 aimed through the fluid 14 at a reflector 40 supported at a selected distance by suitable support members 42 so as to define a flow-measuring acoustic transit time path 44 that, when the angular setting of the probe is at the desired value, lies in a plane containing the axis 16 of the pipe. As will be clear to those who read the complete disclosure here provided, the flow rate detector is used in conjunction with a pipe size detector 46 that employs other transit-time measurements to accurately determine the inside diameter (shown as "D" in FIG. 3) of the pipe 12. The preferred flow rate detector 34 is also of the transit time variety, which allows some portions of the circuitry to be shared for processing outputs of the two detectors. However, it should be clear that any other type of flow detector that is compatible with probe mounting can be used with the pipe size detector 46 and that these include, but are not limited to, turbine sensors, moving target sensors, and electromagnetic or Faraday sensors.

A pipe size detector 46 of the invention, as noted above, is operable to yield a transit time output from which the diameter D of the pipe 12 can be calculated. In one embodiment the detector comprises a pair of size-measuring transducers 50 (distinct from whatever set of transducers may be used for flow measurement) disposed on the sensing head 18 and oriented so as to generate an acoustic size-measuring beam perpendicular to the flow measurement direction 32. During operation of an exemplar pipe size detector 46, one of the transducers 50 projects a short burst of ultrasonic energy, which may comprise sixteen cycles of a 4 MHz signal, along a multi-segment path 54 toward the wall of the pipe. When placed in a pipe full of fluid, the acoustic beam can be reflected multiple times from an internal surface 52 of the pipe 12 to define a complete acoustic path 54, the total length of which can be derived immediately from a measurement of the transit time. Those skilled in the acoustic arts will recognize that the multi-segment path 54 is depicted, in the interest of clarity of presentation, as a single line—i.e., the center line of the beam—and that dispersion of the beam about the center line is ignored.

In one embodiment of the pipe size detector 46, the transducers 50 were oriented to transmit and receive initially horizontal acoustic beams reflected three times from the inner surface 52 of the pipe, as depicted in FIG. 2. In a pipe 12 having a conventional round cross section, these transducers 50 are depicted as having an insertion depth of 25% of the pipe diameter, D. This choice of position provided an acoustic path 54, which essentially formed an equilateral triangle in a plane transverse to the axis of the pipe. As noted previously, many other path geometries are possible, and tests have shown that a four-reflection "square" path 54a between transducers 50 oriented perpendicular to the probe axis at an insertion depth of 13.3% of the pipe ID also provides good results by using a substantially longer path with one more reflection than is found when the triangular path is used.

Those versed in the flow measurement arts will recognize that, in the depiction of FIG. 2, the flow rate detector 34 may project too far into the pipe cross section to provide the optimum volumetric flow rate accuracy. This is because fluid friction with the walls of the pipe slows the velocity of that fluid with respect to the more centrally located fluid so that a flow probe inserted closer to the pipe wall provides a better approximation of the volumetric flow rate over a wide range of flow rates. This depth is usually between 11% and 15% of the pipe diameter for larger pipe sizes and can be up to 50% for smaller pipe sizes, depending on the operating conditions and type of sensor used. To accommodate this range of insertion depths, the pipe size measurement transducers 50 may be mounted at the same level as, or below the flow rate detector 34 or at another location on the sensing head 18, rather than always being at the depicted positions above the flow rate detector. Alternatively, it may be more convenient to keep the size detector 46 on top of the flow rate detector and merely tilt the transducers 50 to produce a different acoustic path, as shown in FIG. 3.

Moreover, although the foregoing discussion describes arrangements using a pair of transducers to measure the transit time along a selected path within a pipe, this measurement could also be made in a pulse-echo mode by using a single transducer, the signal from which would be reflected by a reflector disposed on the sensing head 18 so that a portion of the initial signal could be detected by the single pulse echo transducer. Those skilled in the art will recognize that in this case the acoustic path is twice as long as that previously described with respect to the measurement using two transducers, which may be of interest in some cases. Also, it will be recognized that this pulse-echo mode of operation inherently has a higher signal attenuation, which may be problematic.

The arrangements described above operate for selected combinations of transducer angles, rotational setting of the probe stem, insertion depths and pipe sizes and depend on these parameters being chosen so as to form a closed acoustic path in a plane perpendicular to the axis of the pipe. If the probe stem is at an incorrect angular setting the acoustic beam will spiral down the pipe rather than being reflected to a receiving transducer. Correspondingly, if the insertion depth is slightly different than the selected one, the multiply reflected acoustic beam largely misses the receiving transducer. The reader should recognize that there may be more than one insertion depth within a pipe at which a readily detectable signal will be found. A means of dealing with this issue will be discussed later in this disclosure.

The requirement for precise positioning is a positive aid during installation of a sensing head of the invention. As the probe approaches the optimum location in both depth and angle with respect to the central axis of the pipe, the magnitude of the received acoustic transit time signal rapidly increases. The rate of change of this signal depends upon several factors such as the beam angle, the alignment of the transducers and the condition of the pipe's reflective surface. In an implementation of the invention where the probe transducers were 0.200" wide, 0.125" high and 0.020" thick, and the probe was located in a circular section simulating 8" pipe, a probe insertion depth variation of about 0.050" from the optimum depth produced a received acoustic signal variation of 50%, thus providing the installer with a usable insertion depth tolerance value. A probe rotation of about five degrees from the optimum alignment with the central axis of the pipe also produced a received acoustic signal variation of 50%., thus providing the installer with a rotational tolerance value. This order of sensitivity to mechanical positioning of the probe is, from the perspective of personnel installing the probe, a good balance between locating the approximate insertion position and then making fine adjustments for its optimization.

Figure 4:
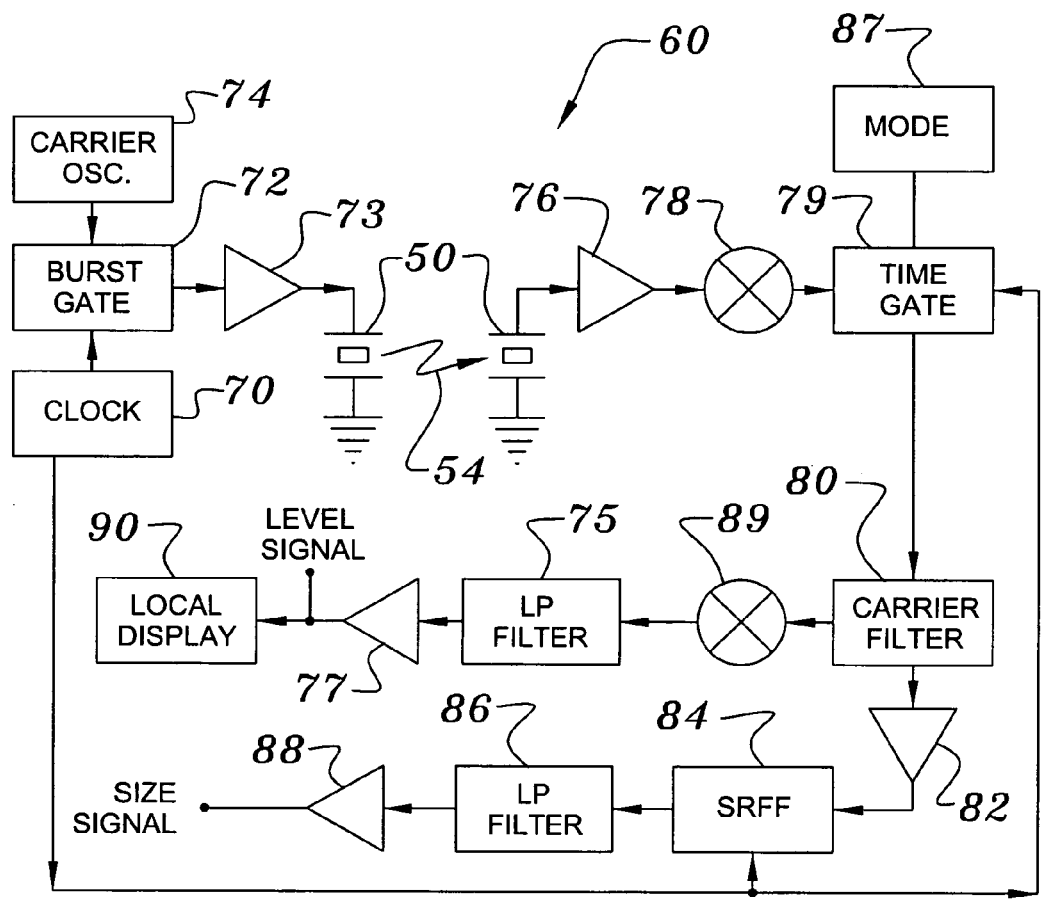
FIG. 4 is a simplified block diagram of a size signal processing circuit of the invention.
Figure 5:
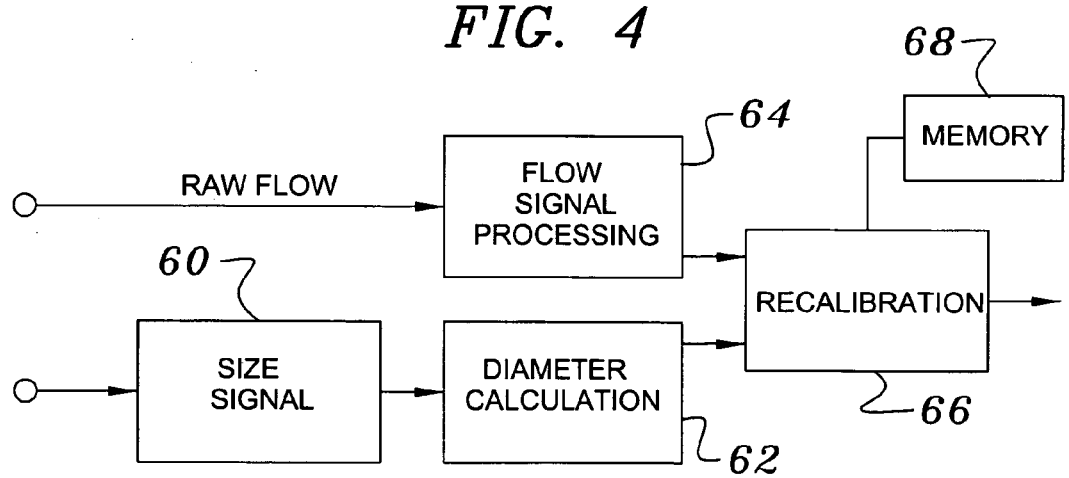
FIG. 5 is a flow chart of a process using an output from the size sensing circuit to calibrate a flow measurement.

Turning now to FIG. 4, one finds a block diagram of a signal processing circuit 60 using the principles of ultrasonic distance detection for the present invention. Because the circuit 60 processes a signal used on an ongoing basis to yield a measure of the actual pipe size, this circuit is hereinafter referred to as a "size signal processing circuit". However, because the same size signal is also used to determine optimal orientation of the probe about its axis and to set the probe at a desired depth, the circuit 60 could also be called an 'installation circuit' or the like.

In the depicted size signal processing circuit 60 a clock 70 provides a series of low frequency pulses, typically at 100 Hz, to an SR-type flip flop 84 to set it to its high state; to a burst gate 72; and to a time gate switch 79. This enables a carrier oscillator 74 signal, which is typically at 4 MHz for the transducers 50 having the exemplar dimensions described above, to be routed to a drive amplifier 73 for the duration of each pulse. The output from the drive amplifier 73 powers a transmitting one of the transducer 50 to generate an acoustic beam that reflects around the inside of a pipe. The fraction of the acoustic beam reaching a receiving one of the transducers 50 is converted into corresponding electrical signals which are amplified by a front-end amplifier 76, detected in magnitude by a detector 78 and, if the time gate switch 79 is closed, filtered by a carrier filter 80 prior to being amplified by an intermediate amplifier 82 to provide a signal that resets the SR flip flop 84 to its low state. Thus, the time that the SR flip flop 84 is in its high state corresponds to a transit time of the acoustic beam 54 and therefore provides a quantitative measure of pipe size. The output from the SR flip flop 84 is preferably filtered by a low pass output filter 86 and amplified by an output amplifier 88 to provide the output pipe size signal for correcting the span measurement of the flow rate sensor and for any other use desired. It should be recognized that there are many other ways of providing the transit time measurement that do not involve the exemplar flip-flop arrangement. These include, but are not limited to, arrangements for turning a digital counter on and off and using the accumulated counts as a direct digital measure of the transit time.

In order to aid in installation of the probe 10, the output from the carrier filter 80 is also peak detected by an installation detector 89 and, after filtering by an installation low pass filter 75, amplified by an installation output amplifier 77 to provide an installation signal, which is preferably a DC signal, with a level responsive to the received electrical size signal strength. This DC signal is used by a local monitoring apparatus, which may be a visual display 90, to assist installation of the probe and can also be used remotely for maintenance or any other use.

It may be noted that carrier filters are characterized by having relatively fast response to quickly reset the SR flip flop or for detecting a peak signal level while low pass filters are characterized by having a relatively slow response to condition a DC signal for display or data processing.

In preferred embodiments, a probe will be preset to generate a single selected measurement path (e.g., one of a square or an equilateral triangle) in a single selected nominal pipe size. The expected diameter range of actual pipes having the selected nominal size will thus define minimum and maximum transit times that the equipment must be able to measure. In some embodiments of the size signal processing circuit, the time gate switch is closed only for an interval encompassing these minimum and maximum values. In other embodiments, as will be discussed later herein, the interval during which the time gate switch 79 is closed can be scanned under operator control, as is schematically indicated in the drawing with a mode control 87.

The precise positioning provided by the present invention provides a further benefit in avoiding erroneous volumetric flow measurements associated with improper probe positioning. In some cases (e.g., a fairly large pipe surrounded by a thick thermal insulation blanket), the purchaser of a flow instrument specifies an incorrect initial probe calibration (e.g., orders a probe calibrated for a 10 inch pipe when the actual diameter is 8 inches, or, more commonly, orders a probe for a Schedule 40 pipe when the actual pipe being used has the same nominal outer size, but is a Schedule 80 pipe). If this probe is installed without benefit of the size measurement apparatus and method of the present invention, inaccurate flow readings are obtained. On the other hand, if the probe comprises size measurement capability, and its installation into an incorrect pipe size is attempted, the installer using the monitoring apparatus will not find a usable size signal magnitude when he or she pushes the probe into the pipe to a depth approximately equal to the predetermined insertion depth and turns it to the approximate angular orientation, thus providing a positive indication that a gross error of some sort has occurred.

It is anticipated that the time gate will have an initial, factory-set interval appropriate for a specified ID of a specified pipe. In some embodiments of the invention, if a gross error or mismatch is found during installation, the installer can use a mode control 87 to cause the time gate interval to reset to a different nominal pipe size, after which the installation could be re-attempted. It is expected that after several trials the appropriate size would be found and all necessary parts of the flow measurement equipment could then be re-programmed to match the newly established nominal diameter.

In preferred embodiments using time gate signal processing, the monitoring apparatus can be relatively simple inasmuch as a high signal level is obtained only when the probe is correctly installed. In cases not using time gated signal processing, an installer could encounter multiple maxima in the output signal (e.g., as might be generated by multiple beam paths as the probe was inserted), in which case a more complex monitoring apparatus, such as a sonar A-scope, might be needed. In general, regardless of the complexity of the installation test equipment, that equipment is expected to be readily removable after installation is complete. Although the preferred monitoring apparatus comprises a visual display that is removable from the sensor after installation is complete, one may note that many other sorts of monitoring apparatuses, including those that supply an audible or tactile output, may also be used with the invention.

The output size signal magnitude from the processing circuit can be immediately used by a diameter calculating circuit or algorithm 62 to provide an accurate measure of the inside diameter, D, of the pipe. For example, in the depiction of FIG. 2, the transit time of the acoustic beam 54 yields, except for a correction associated with the finite width of the sensing head 18, three times the leg length of an equilateral triangle inscribed in a circle, thus indicating that the diameter is two times the leg length divided by the square root of three. The reader will recognize that many different paths can be chosen, and that the exact nature of the diameter calculation will vary accordingly.

In one arrangement for using the invention, the raw flow signal from the flow detector 34 is processed by suitable circuitry 64 or algorithms to yield a flow rate corresponding to a selected nominal pipe diameter. This flow rate, which may correspond to a factory calibration, can then be combined with the measured internal diameter D to derive a more accurate actual flow rate by a suitable re-calibration circuit 66 or algorithm.

Moreover, because the diameter can be easily re-measured from time to time, and because a decrease in the measured diameter can be indicative of dirt or scaling inside the pipe, one can store a value of the diameter in a suitable memory 68 at the beginning of a monitoring period and, later on, at the end of the monitoring period, compare the stored value with a then-current value. If the difference exceeds a selected threshold value, the apparatus can provide a suitable alerting or alarm message to a user of the apparatus to inform him or her that maintenance may be required. Those skilled in the art will recognize that one may make many choices as to the physical location and the type of memory that is used and that one could readily configure a measurement system in which the memory could be located at a central control room containing a computer programmed to track temporal variations in ID for a number of pipes in whatever flow system is being used. Moreover, it will be recognized that many means of making the comparison between the stored and current values are known in the electronic arts.

It will also be recognized that because many materials that deposit on the inside of pipes have a substantially lower acoustic reflectivity than does a metal pipe, one could also store a value of the transit time signal magnitude, rather than the calculated diameter, for comparison a later similar measurement in order to detect fouling of the pipe.

Moreover, the utility of the apparatus of the invention for monitoring the build-up of scaling or internal deposits in a pipe is independent of whatever other, if any, sensing mechanisms are employed on the probe. For example, the transit time size detector of the invention could be used alone on a probe inserted into a tubular portion of a heat exchanger to monitor the build-up of deposits that might degrade the efficiency of the heat exchanger.

It is important for the transducers and the supporting circuitry to respond acoustically and electrically very quickly to the bursts of signal being used because a relatively slow response may result in intolerable transit time measurement error. For example, if the receiving and transmitting transducers are inserted to 25% of the diameter of an 8" pipe filled with water at room temperature, the acoustic transit time is about 340 microseconds. A transit time detection circuit, including the resonant effects of the transducers, introduces measurement errors that are typically under 1 microsecond (⅓%) and would likely be acceptable. If, however, the pipe size is reduced to a 2" diameter, that error increases (to over 1%) and may become intolerable. In such cases, the error may be reduced by using some combination of a higher carrier frequency, very fast rise time transmitting pulses and wave shaping circuits, and carrier phase detection techniques to increase measurement resolution.

Those accustomed to dealing with acoustic transit time measurements will appreciate that the measured transit time is affected by factors such as type of fluid and its temperature. Thus, one may need to compensate for these effects in order to optimize the flow sensing span correction and to calibrate the flow measurement for situations other than those used for the factory flow rate calibration.

Those skilled in the art can now appreciate from the foregoing description that the teaching of the present invention can be implemented in a variety of forms combining a flow probe with a pipe size detector and installation aid. Therefore, while this invention has been described in connection with particular examples thereof, the true scope of the invention should not be limited since other modifications will become apparent to the skilled practitioner upon a study of the drawings, specifications and claims.

What is claimed is:

1. A volumetric flow sensor for measuring a volumetric flow rate of a fluid flowing in a pipe, the sensor comprising:
    a probe insertable into the pipe to a selected insertion depth therein, the probe comprising:
    a flow velocity detector for supplying a raw flow signal responsive to a component of the fluid flow in a selected flow measurement direction defined with respect to an axis of the probe; and
    a pipe size detector for supplying a electrical transit time signal, the pipe size detector comprising at least one acoustic transducer disposed on the probe for projecting an acoustic beam in a direction perpendicular to the flow measurement direction and for detecting a portion of the beam reflected from at least three different locations on an internal surface of the pipe;
    a size signal circuit for processing the transit time signal from the pipe size detector and for generating therefrom a size signal output representative of an inside diameter of the pipe; and
    a flow measurement circuit operable to receive the size signal output and the raw electrical flow signal and to calculate therefrom the volumetric flow rate.

2. The volumetric flow sensor of claim 1 wherein the size signal processing circuit further comprises a time-gate switching element operable to prohibit processing of the transit time signal unless the flow probe is inserted to within an insertion dept tolerance value of the selected insertion depth, and the flow measurement direction is aligned with an axis of the pipe within a rotational tolerance value.

3. The volumetric flow sensor of claim 1 wherein the pipe size detector comprises two acoustic transducers.

4. The volumetric flow sensor of claim 1 wherein the flow velocity detector is an acoustic transit time flow sensing device.

5. The volumetric flow sensor of claim 1 wherein the insertion depth is selected so that the acoustic beam, when projected, reflects from exactly three locations, thereby defining a triangular path.

6. The volumetric flow sensor of claim 1 wherein the insertion depth is selected so that the acoustic beam, when projected, reflects from exactly four locations, thereby defining a square path.

7. An apparatus for installing an insertion probe into a pipe having an inside diameter within a selected diameter range, the apparatus comprising:
    at least one acoustic transducer disposed on the probe for projecting an acoustic beam in a direction perpendicular to an axis of the pipe and for detecting a portion of the beam reflected from at least three different locations on an internal surface of the pipe, the at least one acoustic transducer for supplying a transit time signal within a transit time range characteristic of the inside diameter;
    a signal processing circuit comprising a time gate switch controllable to select only those transit time signals within the defined transit time range, the signal processing circuit for providing an installation signal representative of a magnitude of the selected transit time signals; and
    a display for displaying the installation signal.

8. The apparatus of claim 7 wherein the insertion probe further comprises a flow velocity detector.

9. The apparatus of claim 7 comprising two acoustic transducers.

10. The apparatus of claim 7 further comprising a size signal circuit for processing the transit time signal from the pipe size detector and for generating therefrom a size signal output representative of the inside diameter of the pipe.

11. The apparatus of claim 7 further comprising a memory for storing the magnitude of the selected transit time signal.

12. A method of inserting an insertion probe calibrated for insertion to a selected insertion depth in a pipe having an inside diameter and an axis, the probe having a probe axis that, when the probe is inserted, is perpendicular to the pipe axis, the method comprising:
    a) providing at least one acoustic transducer disposed on the probe, the at least one acoustic transducer projecting an acoustic beam that defines a multi-segment path characterized by an acoustic transit time within a defined transit time range only if the inside diameter of the pipe is within a selected diameter range, the probe is inserted to the selected insertion depth, and the probe is turned about the probe axis into a setting in which the acoustic beam is projected perpendicular to the pipe axis, the at least one acoustic transducer supplying electrical size signals responsive to transit times of the beam;

b) providing a signal processing circuit comprising a time gate switch controlled to select only those electrical size signals corresponding to the defined transit time range, the signal processing circuit providing an installation signal having a magnitude representative of a magnitude of the selected electrical size signals;

c) aligning the insertion probe so that the at least one transducer is aligned, within a rotational tolerance value, perpendicular to the axis of the pipe;

d) inserting the probe into the pipe along the probe axis to a depth within a depth tolerance value of the selected insertion depth;

e) monitoring the installation signal and:

f) if the installation signal magnitude is above a first selected value, both moving the probe along the probe axis and turning it thereabout until the installation signal magnitude attains a maximum value; and g) if the installation signal magnitude is not above the first selected value, determining that the inside diameter of the pipe is not within the selected range.

13. The method of claim 12 wherein the probe comprises a flow velocity detector for supplying a raw flow signal output responsive to a rate at which fluid flows along a flow measurement direction perpendicular to the probe axis.

14. The method of claim 12 further comprising providing a local visual display removably electrically attachable to the signal processing circuitry and wherein monitoring the magnitude of the installation signal comprises viewing a representation thereof on the local visual display.

15. The method of claim 12 further comprising steps taken after determining that the diameter of the pipe is not within the selected range of:

h) controlling the time gate switch to select a second range of transit times corresponding to a second range of inside diameters; and i) repeating steps c) through f).

16. A method of measuring a volumetric flow rate in a pipe having a pipe axis, the method comprising the steps of:

a) providing a probe having a probe axis, the probe comprising:

a flow velocity detector supplying a raw flow signal responsive to a rate at which fluid flows along a flow measurement direction perpendicular to the probe axis; and a pipe size detector supplying a size signal responsive to a transit time of an acoustic beam projected in a selected direction perpendicular to the flow measurement direction;

b) inserting the probe into the pipe so that the flow measurement direction is parallel to the axis of the pipe and so that the acoustic beam is reflected a selected number of times, the selected number being at least two, from an inside surface of the pipe;

c) calculating the diameter of the pipe from the size signal; and d) calculating, from the calculated diameter of the pipe and the raw flow signal, the volumetric flow rate.

17. The method of claim 16 further comprising storing, at a first time, a first value of the calculated diameter; and comparing, at a second time later than the first time, the stored first value of the calculated diameter with the value of the calculated diameter calculated at the second time.

18. The method of claim 16 wherein the selected direction in which the pipe size detector projects an acoustic beam is perpendicular to the axis of the probe.

19. The method of claim 16 wherein the beam is reflected three times from the inside surface of the pipe.

20. The method of claim 16 wherein the beam is reflected four times from the inside surface of the pipe.

21. The method of claim 16 wherein the raw flow signal comprises a transit time flow signal.

22. A method of monitoring a change in an inside diameter of a pipe over a period of time during which a fluid flows through the pipe, the method comprising:

providing at least one acoustic transducer disposed on a probe inserted into the pipe, the at least one acoustic transducer projecting an acoustic beam in a direction perpendicular to an axis of the pipe and detecting a portion of the beam reflected from at least two different locations on an internal surface of the pipe, the at least one acoustic transducer supplying a transit time signal within a transit time range characteristic of the inside diameter;

providing a signal processing circuit comprising a time gate switch controlled to select only those transit time signals within the defined transit time range, the signal processing circuit providing a monitoring signal representative of the selected transit time signals;

storing a beginning value of the monitoring signal at a beginning of the period of time;

comparing the beginning value of the monitoring signal with a then current value of the monitoring signal at the end of the period of time to determine a difference therebetween.

23. The method of claim 22 further comprising supplying a message to an operator if the difference between the values is more than a selected amount.

24. The method of claim 22 wherein the monitoring signal is representative of the inside diameter of the pipe.

25. The method of claim 22 wherein the monitoring signal comprises a signal representative of a magnitude of the selected transit time signals.

\* \* \* \* \*